(12) United States Patent
Skrzypczynski et al.

(10) Patent No.: US 8,552,173 B2
(45) Date of Patent: Oct. 8, 2013

(54) COMPOSITIONS, PROBES, AND CONJUGATES AND USES THEREOF

(75) Inventors: Zbigniev Skrzypczynski, Verona, WI (US); Sarah R. Wayland, Madison, WI (US)

(73) Assignee: Third Wave Technologies, Inc., Madison, WI (US)

( * ) Notice: Subject to any disclaimer, the term of this patent is extended or adjusted under 35 U.S.C. 154(b) by 0 days.

(21) Appl. No.: 13/214,948

(22) Filed: Aug. 22, 2011

(65) Prior Publication Data

US 2012/0010395 A1    Jan. 12, 2012

Related U.S. Application Data

(62) Division of application No. 12/714,983, filed on Mar. 1, 2010, now Pat. No. 8,003,771, which is a division of application No. 11/805,038, filed on May 22, 2007, now Pat. No. 7,674,924.

(60) Provisional application No. 60/802,397, filed on May 22, 2006.

(51) Int. Cl.
*C07H 21/00* (2006.01)
*C12Q 1/68* (2006.01)
*C07H 21/04* (2006.01)

(52) U.S. Cl.
USPC ....... 536/25.3; 536/23.1; 536/24.3; 536/26.6; 435/6.1

(58) Field of Classification Search
USPC .................. 536/23.1, 24.3, 25.3, 26.6; 435/6
See application file for complete search history.

(56) References Cited

U.S. PATENT DOCUMENTS

| 4,683,195 A | 7/1987 | Mullis |
| 4,683,202 A | 7/1987 | Mullis |
| 4,775,619 A | 10/1988 | Urdea |
| 4,876,187 A | 10/1989 | Duck |
| 4,965,188 A | 10/1990 | Mullis |
| 5,011,769 A | 4/1991 | Duck |
| 5,118,605 A | 6/1992 | Urdea |

(Continued)

FOREIGN PATENT DOCUMENTS

| WO | WO97/27214 | 7/1997 |
| WO | WO98/42873 | 10/1998 |
| WO | WO99/67641 | 12/1999 |
| WO | WO00/39587 | 7/2000 |

OTHER PUBLICATIONS

Beaucage, et al. "The Functionalization of Oligonucleotides Via Phosphoramidite Derivatives" Tetrahedron, vol. 49, pp. 1925-1963 (1993).
Berry & Associates "5-Ethynyl-dU CEP" Product Details Web Page.

(Continued)

*Primary Examiner* — Jezia Riley
(74) *Attorney, Agent, or Firm* — Casimir Jones, S.C.

(57) ABSTRACT

The present invention relates to compositions useful as probes and in other applications and methods of their use. In some embodiments, nucleotides are prepared and functionalized with dyes. In some embodiments a first molecule is functionalized with an alkynyl group, a second molecule is functionalized with an azide group, and said first and second molecules are mixed under conditions to form a conjugate with a 1,2,3-triazol group. In further embodiments, a nucleotide is functionalized with an alkynyl group, a dye is functionalized with an azide group, and mixing the nucleotide and the dye forms a conjugate capable of emitting light.

15 Claims, 8 Drawing Sheets

(56) References Cited

U.S. PATENT DOCUMENTS

| | | | |
|---|---|---|---|
| 5,210,015 A | 5/1993 | Gelfand |
| 5,403,711 A | 4/1995 | Walder |
| 5,427,930 A | 6/1995 | Birkenmeyer |
| 5,474,796 A | 12/1995 | Brennan |
| 5,494,810 A | 2/1996 | Barany |
| 5,601,980 A | 2/1997 | Gordon |
| 5,700,637 A | 12/1997 | Southern |
| 5,846,717 A | 12/1998 | Brow |
| 5,858,659 A | 1/1999 | Sapolsky |
| 5,876,675 A | 3/1999 | Kennedy |
| 5,882,465 A | 3/1999 | McReynolds |
| 5,882,867 A | 3/1999 | Ullman |
| 5,925,525 A | 7/1999 | Fodor |
| 5,952,174 A | 9/1999 | Nikiforov |
| 5,976,336 A | 11/1999 | Dubrow |
| 5,985,551 A | 11/1999 | Brennan |
| 5,985,557 A | 11/1999 | Prudent |
| 5,994,069 A | 11/1999 | Hall |
| 6,001,311 A | 12/1999 | Brennan |
| 6,001,567 A | 12/1999 | Brow |
| 6,017,696 A | 1/2000 | Heller |
| 6,040,193 A | 3/2000 | Winkler |
| 6,045,996 A | 4/2000 | Cronin |
| 6,046,056 A | 4/2000 | Parce |
| 6,051,380 A | 4/2000 | Sosnowski |
| 6,068,752 A | 5/2000 | Dubrow |
| 6,068,818 A | 5/2000 | Ackley |
| 6,100,541 A | 8/2000 | Nagle |
| 6,110,677 A | 8/2000 | Western |
| 6,121,001 A | 9/2000 | Western |
| 6,150,180 A | 11/2000 | Parce |
| 6,167,910 B1 | 1/2001 | Chow |
| 6,171,067 B1 | 1/2001 | Parce |
| 6,182,733 B1 | 2/2001 | McReynolds |
| 6,186,660 B1 | 2/2001 | Kopf-Sill |
| 6,238,538 B1 | 5/2001 | Parce |
| 6,242,266 B1 | 6/2001 | Schleifer |
| 6,251,343 B1 | 6/2001 | Dubrow |
| 6,267,858 B1 | 7/2001 | Parce |
| 6,274,089 B1 | 8/2001 | Chow |
| 6,321,791 B1 | 11/2001 | Chow |
| 6,326,083 B1 | 12/2001 | Yang |
| 6,358,387 B1 | 3/2002 | Kopf-Sill |
| 6,379,974 B1 | 4/2002 | Parce |
| 6,399,397 B1 | 6/2002 | Zarling |
| 6,413,782 B1 | 7/2002 | Parce |
| 6,418,968 B1 | 7/2002 | Pezzuto |
| 6,425,972 B1 | 7/2002 | McReynolds |
| 6,429,025 B1 | 8/2002 | Parce |
| 6,432,720 B2 | 8/2002 | Chow |
| 6,447,727 B1 | 9/2002 | Parce |
| 7,951,926 B2 | 5/2011 | Morvan et al. |
| 2005/0032081 A1 | 2/2005 | Ju et al. |
| 2006/0147963 A1* | 7/2006 | Barone et al. ............ 435/6 |
| 2008/0050731 A1* | 2/2008 | Agnew et al. ............ 435/6 |
| 2009/0124571 A1* | 5/2009 | Morvan et al. ............ 514/44 |

OTHER PUBLICATIONS

Binder, et al. "Directed Nanoparticle Binding onto Microphase-Seprated Block Copolymer Thin Films" Macromolecules, vol. 38, pp. 9405-9410.

Bryan, et al. "Covalent display of oligosaccharide arrays in microtiter plates" J Am Chem Soc. Jul. 21, 2004;126 (28):8640-1.

Cognard "Alignment of Nematic Liquid Crystals and their Mixtures" Mol. Cryst. Liq. Cryst. 1:1 74 (1982).

Collman, et al. "'Clicking' functionality onto electrode surfaces" Langmuir. Feb. 17, 2004;20(4):1051-3.

Devaraj, et al. "Chemoselective covalent coupling of oligonucleotide probes to self-assembled monolayers" J Am Chem Soc. Jun. 22, 2005;127(24):8600-1.

Doty, et al. "Strand Separation and Specific Recombination in Deoxyribonucleic Acids: Physical Chemical Studies" Proc. Natl. Acad. Sci. USA 46:461 (1960).

Glen Research "5'-Hexynyl Phosphoramidite—Conjugate with a Click" Research Report Web Page.

Graham, et al. "Cycloadditions as a Method for Oligonucleotide Conjugation" Current Organic Synthesis, vol. 3, pp. 9-17 (2006).

Hall, et al. "Sensitive detection of DNA polymorphisms by the serial invasive signal amplification reaction" PNAS, USA, 97:8272-7 (2000).

Huang, et al. "The application of quantum dots as fluorescent label to glycoarray" Anal Biochem. May 1, 2005;340(1):52-6.

Kolb, et al. "Click Chemistry: Diverse Chemical Function from a Few Good Reactions" Angew Chem Int Ed Engl. Jun. 1, 2001;40(11):2004-2021.

Kolb, et al. "The growing impact of click chemistry on drug discovery" DDT, vol. 8(24), pp. 1128-1137 (2003).

Ladam, et al. "Protein Adsorption onto Auto-Assembled Polyelectrolyte Films" Langmuir; 2001; 17(3); 878-882.

Link, et al. "Cell surface labeling of *Escherichia coli* via copper(I)-catalyzed [3+2] cycloaddition" J Am Chem Soc. Sep. 17, 2003;125(37):11164-5.

Lyamichev, et al. "Polymorphism identification and quantitative detection of genomic DNA by invasive cleavage of oligonucleotide probes" Nat. Biotech., 17:292-6 (1999).

Marmur, et al. "Strand separation and specific recombination in deoxyribonucleic acids: Biological studies" Proc. Natl. Acad. Sci. USA 46:453 (1960).

Molteni, et al. "1,3-Dipolar cycloadditions of MeOPEG-bounded azides" Tetrahedron, vol. 61, pp. 4983-4987.

Nakane, et al. "Synthesis of cross-linked circular DNAs using Hüisgen reaction" Nucleic Acids Symp Ser (Oxf). 2005 (49): 189-90.

Ostermayer "Preparation and properties of infrared-to-visible conversion phosphors" Metall. Trans. 752, 747-755 [1971].

Perez-Balderas, et al. "Multivalent neoglycoconjugates by regiospecific cycloaddition of alkynes and azides using organic-soluble copper catalyst" Org Lett. May 29, 2003;5(11):1951-4.

Reid, Organic Chemistry of Bivalent Sulfur, vol. 1, pp. 21 29, 32 35, vol. 5, pp. 27 34, Chemical Publishing Co., New York, 1.958, 1963.

Reid, Organic Chemistry of Bivalent Sulfur, vol. 2, pp. 16 21, 24 29, vol. 3, pp. 11 14, Chemical Publishing Co., New York, 1960.

Seela, et al. "DNA Containing Side Chains with Terminal Triple Bonds: Base-Pair Stability and Functionalization of Alkynylated Pyrimidines and 7-Deazapurines" Chemistry & Biodiversity, vol. 3, pp. 509-514 (2006).

Selvin "Fluorescence resonance energy transfer" 1995, Methods Enzymol., 246:300-34.

Seo, et al. "Click chemistry to construct fluorescent oligonucleotides for DNA sequencing" J Org Chem. Jan. 24, 2003;68(2):609-12.

Seo, et al. "Photocleavable fluorescent nucleotides for DNA sequencing on a chip constructed by site-specific coupling chemistry" Proc Natl Acad Sci U S A. Apr. 13, 2004;101(15):5488-93.

Sharpless, at al. "A stepwise huisgen cycloaddition process: copper(I)-catalyzed regioselective "ligation" of azides and terminal alkynes" Angew. Chem. Int. Ed., 2002, 41(14), 2596-9.

Sivakumar, et al. "A fluorogenic 1,3-dipolar cycloaddition reaction of 3-azidocoumarins and acetylenes" Org Lett. Nov. 25, 2004;6(24):4603-6.

Stockert, et al. "Cytochemistry of mast cells: new fluorescent methods selective for sulfated glycosaminoglycans" 2000 Acta. Histochem. 102:259-272.

Stryer, et al. "Fluorescence energy transfer as a spectroscopic ruler" 1978, Ann. Rev. Biochem., 47:819-46.

Sun, et al. "Carbohydrate and protein immobilization onto solid surfaces by sequential Diels-Alder and azide-alkyne cycloadditions" Bioconjug Chem. Jan.-Feb. 2006;17(1):52-7.

Tyagi, et al. "Wavelength-shifting molecular beacons" Nature Biotechnology 18:1191-6 (2000).

Van De Rijke, et al. "Up-converting phosphor reporters for nucleic acid microarrays" Nature Biotechnol. 19(3):273-6 [2001].

Wagner, et al. "Covalent immobilization of native biomolecules onto Au(111) via N-hydroxysuccinimide ester functionalized self-assembled monolayers for scanning probe microscopy" Biophys. J., vol. 70, pp. 2052-2066 (1996).

Wang, at al. "Synthesis of 1H-pyridin-2-one derivatives as potent and selective farnesyltransferase inhibitors" Bioorg Med Chem Lett. Sep. 20, 2004;14(18):4603-6.

Wu, et al. "Multivalent, bifunctional dendrimers prepared by click chemistry" Chem Commun (Camb). Dec. 14, 2005; (46):5775-7.

Zhou, et al. "A fluorogenic probe for the copper(I)-catalyzed azide-alkyne ligation reaction: modulation of the fluorescence emission via $3(n,pi)$-$1(pi,pi)$ inversion" J Am Chem Soc. Jul. 28, 2004;126(29):8862-3.

\* cited by examiner automated synthesis

DNA conjugate

COMPOSITIONS, PROBES, AND CONJUGATES AND USES THEREOF

This application is a divisional of U.S. patent application Ser. No. 12/714,983, filed Mar. 1, 2010, which is a divisional of U.S. Pat. No. 7,674,924, issued Mar. 9, 2010, which claims priority to U.S. Patent Application Ser. No. 60/802,397, filed May 22, 2006, each of which is incorporated herein by reference.

FIELD OF INVENTION

The present invention relates to compositions useful as probes and in other applications and methods of their use. In some embodiments, nucleotides are prepared and functionalized with dyes. In some embodiments a first molecule is functionalized with an alkynyl group, a second molecule is functionalized with an azide group, and said first and second molecules are mixed under conditions to form a conjugate with a 1,2,3-triazol group. In further embodiments, a nucleotide is functionalized with an alkynyl group, a dye is functionalized with an azide group, and mixing the nucleotide and the dye forms a conjugate capable of emitting light.

BACKGROUND

Identification of nucleic acid sequences in living organisms including infectious agents is useful for the diagnosis, prevention, and treatment of many diseases. In many synthetic chemical probes, double-stranded DNA formed by the molecular recognitions of complementary sequences is the primary feature to be identified. In many of these assays, it is desirable to immobilize expensive and difficult to prepare nucleic acid sequences to solid surfaces in order to maximize the potential for reuse. However, verification of the specific placement of the sequences on a solid substrate array can be difficult. Thus, there is a need to develop improved methods of the detection of the placement of probes on an array.

Many probe assays utilize synthetically prepared nucleic acid sequences. Nucleic acid sequences are typically prepared by solid phase synthesis using phosphoramidite derivatives. Direct conjugation of DNA molecules to different materials, such as dyes, sugars, and peptides during solid phase synthesis has practical challenges. Often the material to be conjugated to DNA will be not compatible with the conditions used to synthetically produce DNA through phosphoramidite couplings. Some conventional postsynthetic bioconjugation protocols, including carboxyl-group activation with N-hydroxysuccinimide (NHS)/N,N'-dicyclohexylcarbodiimide (DCC) are at times inefficient, particularly in the case of conjugating dye molecules to DNA. Thus, there is a need to identify improved methods for making conjugates containing nucleic acid sequences compatible with solid-phase synthetic procedures.

SUMMARY OF THE INVENTION

The invention provides compositions useful as probes and in other applications and methods of their use. In some embodiments, nucleotides are prepared and functionalized with dyes. In some embodiments a first molecule is functionalized with an alkynyl group, a second molecule is functionalized with an azide group, and said first and second molecules are mixed under conditions to form a conjugate with a 1,2,3-triazol group. In further embodiments, a nucleotide is functionalized with an alkynyl group, a dye is functionalized with an azide group, and a conjugate capable of emitting light is formed by mixing the nucleotide and the dye functionalized with an azide group in the presence of an appropriate catalyst, if needed.

In some embodiments, the present invention provides protected phosphoramidites having an alkyne group for use in producing labeled nucleic acid molecules. The phosphoramidite may be reacted with a biomolecule (e.g., nucleic acid molecule) to generate a biomolecule having the alkyne group at a terminal end. The alkyne group on the first molecule may be reacted with a second molecule comprising an azide group such that the first molecule and the second molecule are conjugated together. The compositions and methods of the present invention may be used in any application where it is desired to add a biomolecule such as a nucleotide or nucleic acid molecule to another molecule. Such methods can be used, for example, to attached molecules to solid surfaces. One exemplary application is the use of multiple labeled structures comprising reactive alkyne groups affixed to a surface or along a linear polymer that provide interactive attachment points for other components (e.g., nanoparticles, nanocrystals, quantum dots, etc.).

In some embodiments, the present invention provides a method for making a labeled nucleic acid molecule, comprising: providing a dye comprising an azide group and a nucleotide or other biomolecule comprising or linked to an alkynyl group; and mixing the dye and the nucleotide under conditions such that the dye is conjugated to the nucleotide. In some embodiments the dye and/or the nucleotide is attached another molecule or a solid surface. The present invention provides composition generated by such methods. The present invention also provides methods of detecting such compositions comprising: detecting the presence of, absence of, or location of said dye. The present invention is not limited by the nature of the dye. Any moiety that provides a detectable signal may be used.

In some embodiments, the invention provides a method of making a nucleotide conjugate comprising: reacting a nucleotide comprising an ethynyl group with a compound or substrate comprising an azide group. In further embodiments, said nucleotide comprises an azide group and said compound or substrate comprises an ethynyl group. In further embodiments reacting said nucleotide, compound or substrate provides a fluorescent or other detectably labeled conjugate.

In some embodiments, the invention provides a substituted or unsubstituted compound functioning to react with an azide to form a compound with a 1,2,3-triazol group having the following formula:

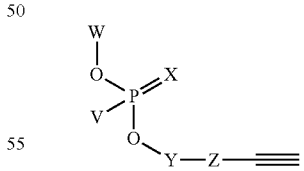

wherein, W is a nucleotide, oligonucleotide, other nucleic acid molecule, or other biomolecule or biopolymer; X is O or S, V is a phosphate protecting group (e.g., OCE, OMe, etc.), Y is absent or a linking group (e.g., —[(CR$_a$R$_b$)$_n$-A-B—C—(CR$_c$R$_c$)$_m$D]$_p$—; R$_a$, R$_b$, R$_c$, and R$_d$ are the same or different and, at each occurrence, independently hydrogen, alkyl, or substituted alkyl; n is 0 to 100; m is 1 to 20; p is 1 to 100; A, B, C, and D are the same or different and, at each occurrence, independently absent, O, S, N, or carbonyl); and Z comprises an aryl group or is absent. In some embodiments, the invention relates to a conjugate functioning to a detectable moiety (e.g., luminescent or fluorescent dye) having the following formula:

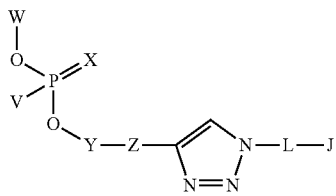

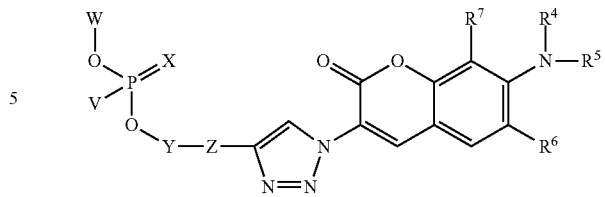

wherein, J is a biomolecule or a solid substrate; and L is a detectable moiety (e.g., a moiety that provides a fluorescent or luminescent signal under reaction conditions).

Such conjugates may be used in any type of detection assay that employs labeled nucleotides, oligonucleotides, or polynucleotides. Exemplary methods are described herein. In some embodiments, the invention provides a composition comprising a substituted or unsubstituted compound selected from the group consisting of: (ethynylaryl)amino-oxo-alkyl-carboxylic acid; N'-(hydroxyalkyl)-N-(ethynylaryl)-alkandiamide; N'-(aminoalkyl alkyl dialkylamidophosphite)-N-(ethynylaryl)-alkandiamide. In further embodiments, the compound comprises: 5-(4-ethynylphenyl)amino-5-oxo-pentanoic acid; N'-(6-hydroxyhexyl)-N-(4-ethynylphenyl)-pentandiamide; or N'-(6-aminohexyl 2-cyanoethyl diisopropylamidophosphite)-N-(4-ethynylphenyl)-pentandiamide.

In some embodiments, the invention provides a substituted or unsubstituted compound functioning to provide a detectable signal having the following formula:

wherein, W is a nucleotide or oligonucleotide or other nucleic acid molecule; $R^4$ and $R^7$ are the same or different and, at each occurrence, independently hydrogen, alkyl, or substituted alkyl; or $R^4$ and $R^7$ taken together with the carbon atom to which they are attached form a homocycle, substituted homocycle, heterocycle or substituted heterocycle; $R^5$ and $R^6$ are the same or different and, at each occurrence, independently hydrogen, alkyl, or substituted alkyl; or $R^5$ and $R^6$ taken together with the carbon atom to which they are attached form a homocycle, substituted homocycle, heterocycle or substituted heterocycle.

In some embodiments, the invention provides a composition comprising a substituted or unsubstituted compound having the following formula:

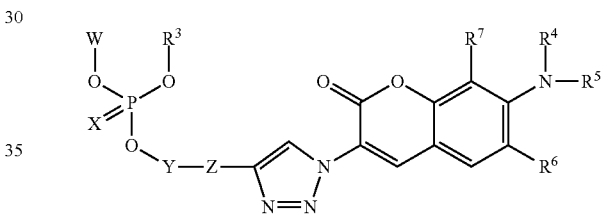

wherein, $R^3$ is hydrogen, alkyl, substituted alkyl, or a protecting group. In further embodiments, the compound has the following formula:

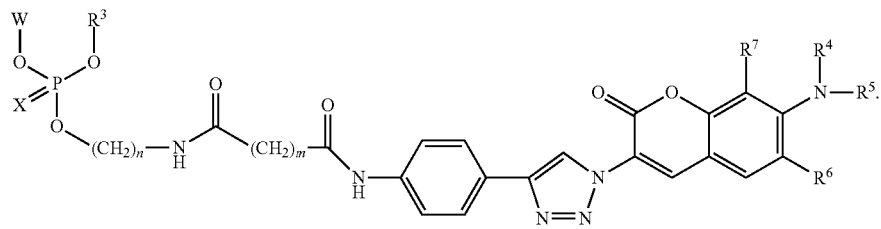

In further embodiments, the compound has the following formula:

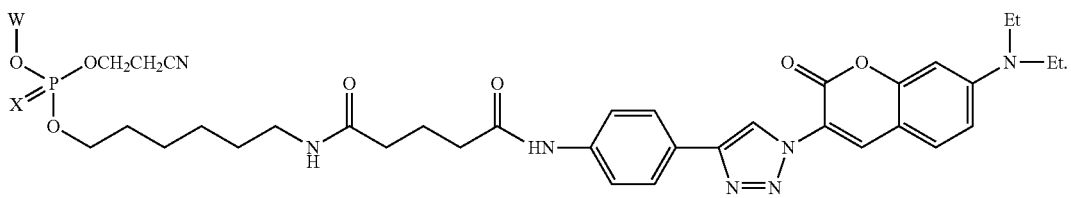

In further embodiments, the compound has the following formula:

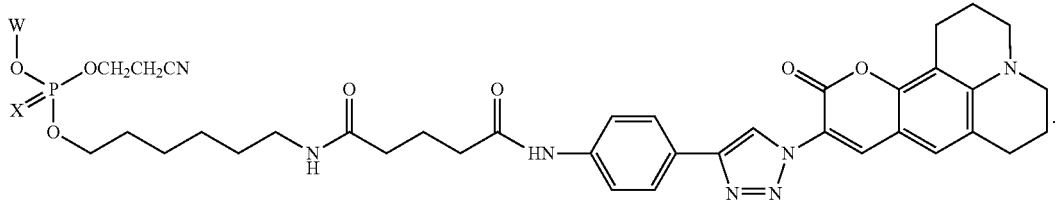

In additional embodiments, the invention relates to a substituted or unsubstituted compound functioning to react with azides to form a compound with a 1,2,3-triazol group having the following formula:

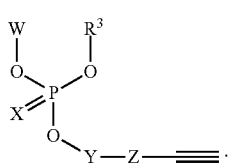

In further embodiments, the substituted or unsubstituted compound has the following formula:

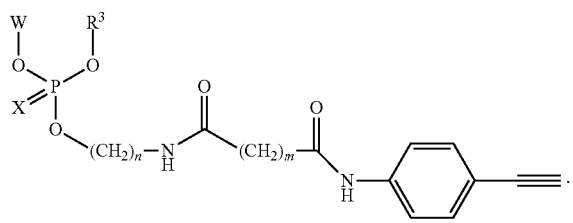

In further embodiments, the compound has the following formula:

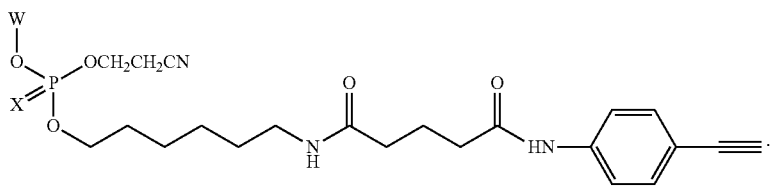

In some embodiments, the invention provides a substituted or unsubstituted compound having the following formula:

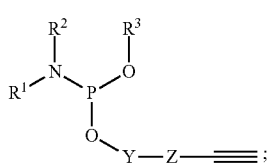

wherein, $R^1$ and $R^2$ are the same or different and, at each occurrence, independently alkyl or substituted alkyl.

In some embodiments, the compounds of the present invention comprise a phosphoramidite configured for the addition of multiple moieties, and containing a terminal alkyne. An example of such a compound has the following formula:

The present invention further provides biomolecules, solid surfaces, etc. that have been reacted with such phosphoramidites.

In some embodiments, the invention provides a method of making a detectably labeled conjugate comprising mixing a substituted or unsubstituted ethynylaryl conjugate of a nucleotide with a compound comprising an azide group under conditions such that a detectably labeled conjugate is formed. In some embodiments, the method of making an ethynylaryl conjugate of a nucleotide comprises mixing a nucleotide with substituted or unsubstituted N'-(aminoalkyl alkyl dialkylamidophosphite)-N-(ethynylaryl)-alkandiamide under conditions such that an ethynylaryl conjugate of a nucleotide is formed.

In further embodiments, the invention provides a method of making (ethynylaryl)amino-oxo-alkylcarboxyloic acid comprising: mixing ethynylaminoaryl with alkyldicarboxylic anhydride under conditions such that (ethynylaryl)amino-oxo-alkylcarboxylic acid is formed.

In some embodiments, the invention provides a method of making N'-(hydroxyalkyl)-N-(ethynylaryl)-alkandiamide comprising i) mixing (ethynylaryl)amino-oxo-alkylcarboxylic acid with a reagent under conditions such that a compound comprising is formed and ii) mixing said compound comprising with a hydroxyaminoalkyl under conditions such that N'-(hydroxyalkyl)-N-(ethynylaryl)-alkandiamide is formed.

In some embodiments, the invention provides a method of making a substituted or unsubstituted N'-(aminoalkyl alkyl dialklyamidophosphite)-N-(ethynylaryl)-alkandiamide comprising mixing N'-(hydroxyalkyl)-N-(ethynylaryl)-alkandiamide with substituted or unsubstituted alkyl-N,N,N',N'-tetraalkylphosphoramidite under conditions such that N'-(aminoalkyl alkyl dialklyamidophosphite)-N-(ethynylaryl)-alkandiamide is formed.

In additional embodiments, the invention provides a method of making 5-(4-ethynylphenyl)amino-5-oxo-pentanoic acid comprising: mixing 4-ethynylaniline with glutaric anhydride under conditions such that 5-(4-ethynylphenyl)amino-5-oxo-pentanoic acid is formed.

In some embodiments, invention provides a method of making N'-(6-hydroxyhexyl)-N-(4-ethynylphenyl)-pentandiamide comprising: i) mixing 5-(4-ethynylphenyl)amino-5-oxo-pentanoic acid with N-hydroxysuccinimide under conditions such that (2,5-dioxopyrrolidin-1-yl) 5-(4-ethynylphenyl)amino-5-oxo-pentanate is formed and ii) mixing (2,5-dioxopyrrolidin-1-yl) 5-(4-ethynylphenyl)amino-5-oxo-pentanate with 1-amino-6-hexanol under conditions such that N'-(6-hydroxyhexyl)-N-(4-ethynylphenyl)-pentandiamide is formed. In further embodiments the method of making N'-(6-hydroxyhexyl)-N-(4-ethynylphenyl)-pentandiamide comprises i) mixing 5-(4-ethynylphenyl)amino-5-oxo-pentanoic acid with a reagent under conditions such that a compound is formed and ii) mixing said compound with 1-amino-6-hexanol under conditions such that N'-(6-hydroxyhexyl)-N-(4-ethynylphenyl)-pentandiamide is formed.

In some embodiments, the invention provides a method of making N'-(6-aminohexyl 2-cyanoethyl diisopropylamidophosphite)-N-(4-ethynylphenyl)-pentandiamide comprising mixing N'-(6-hydroxyhexyl)-N-(4-ethynylphenyl)-pentandiamide with 2-Cyanoethyl-N,N,N',N'-tetraisopropylphosphoramidite under conditions such that N'-(6-aminohexyl 2-cyanoethyl diisopropylamidophosphite)-N-(4-ethynylphenyl)-pentandiamide is formed.

In additional embodiments, the invention provides purified and isolated forms of compounds disclosed herein including those essentially free of normal contaminants. In further embodiments, the invention relates to kits comprising compositions disclosed herein and/or kits to perform method disclosed herein.

DETAILED DESCRIPTION OF THE INVENTION

Figure 1:
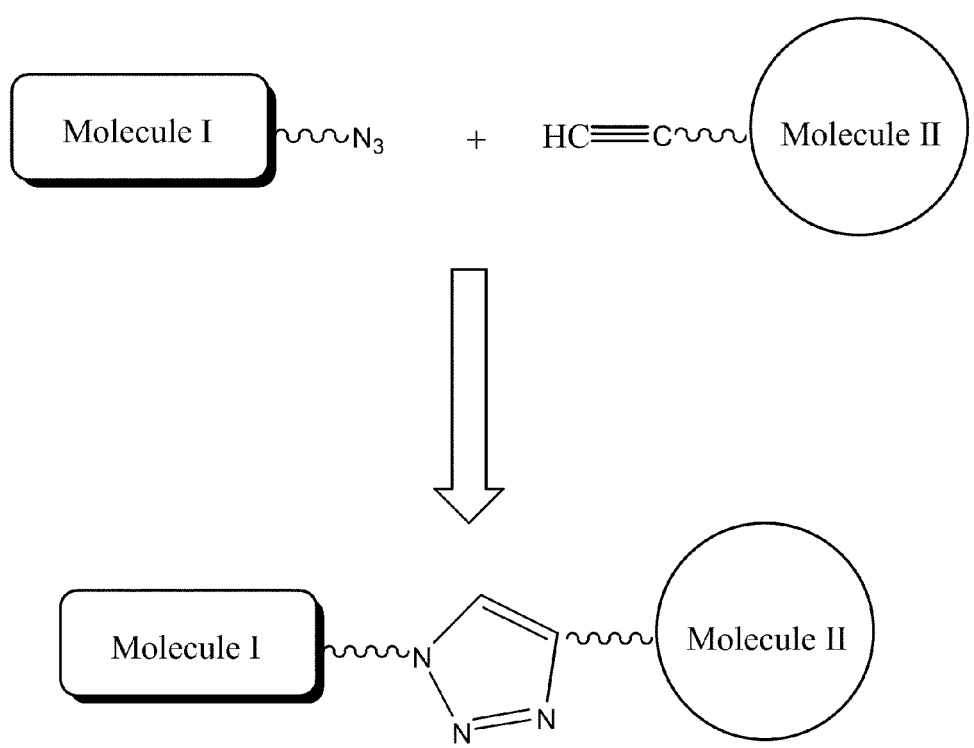
FIG. 1 illustrates formation of a conjugate by mixing a molecule containing an azide and a molecule containing an ethynyl group under conditions such that a 1,2,3-triazole is formed.
Figure 2:
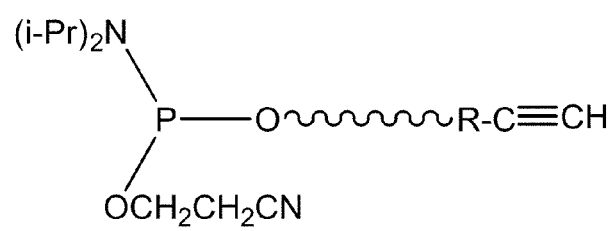
FIG. 2 illustrates formation by automated synthesis of a molecule containing a phosphoamidite and nucleic acid sequence capable of forming a conjugate.
Figure 2:
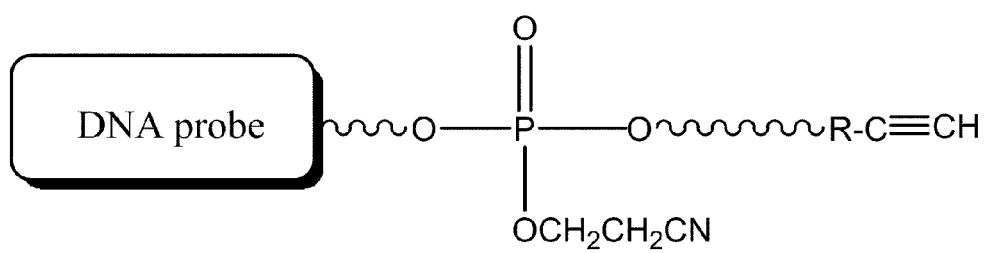
Figure 3:
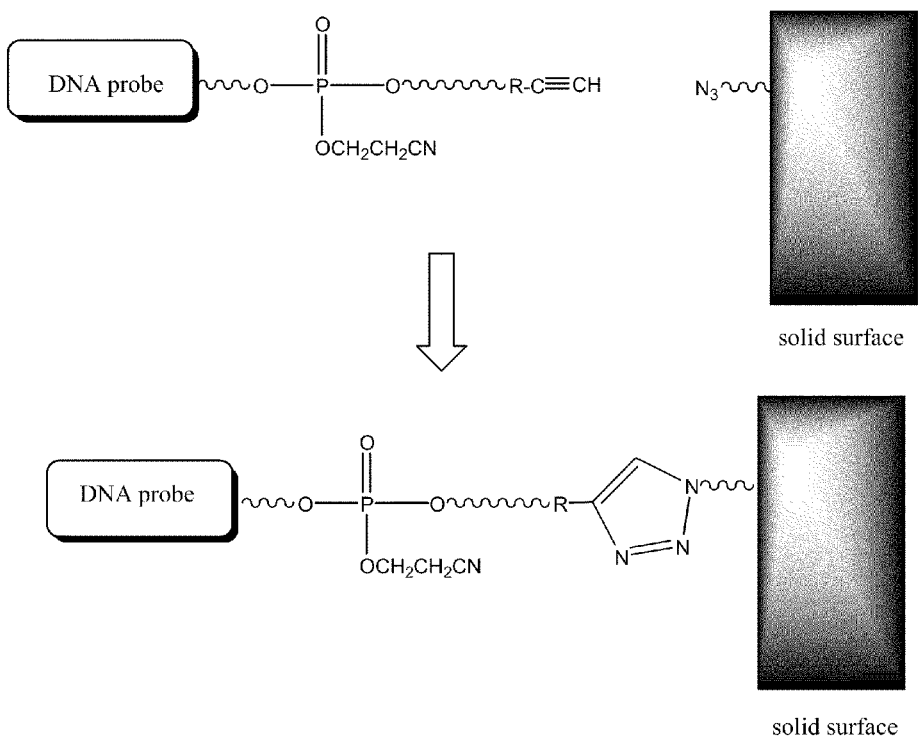
FIG. 3 illustrates immobilization of a probe to solid substrate.
Figure 4:
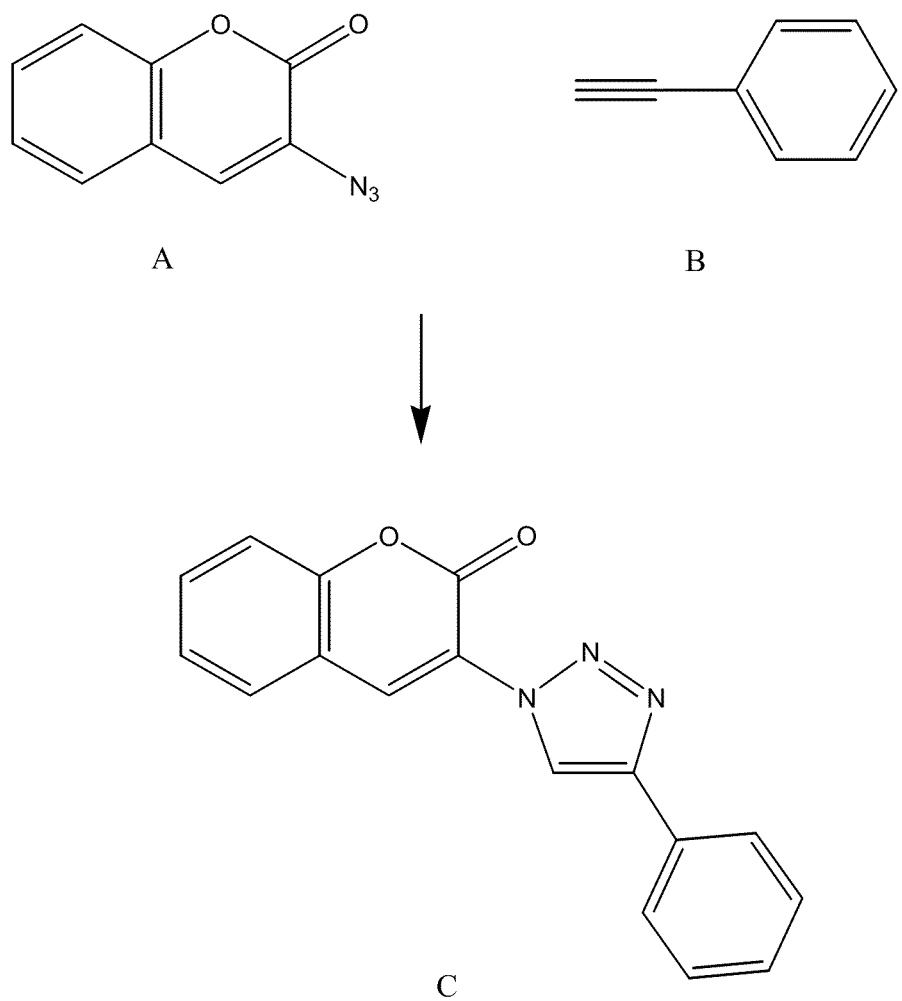
FIG. 4 illustrates formation of a fluorescent compound with a 1,2,3-triazol group by mixing a compound B with an ethynyl group and a compound A with an azide group.
Figure 5:
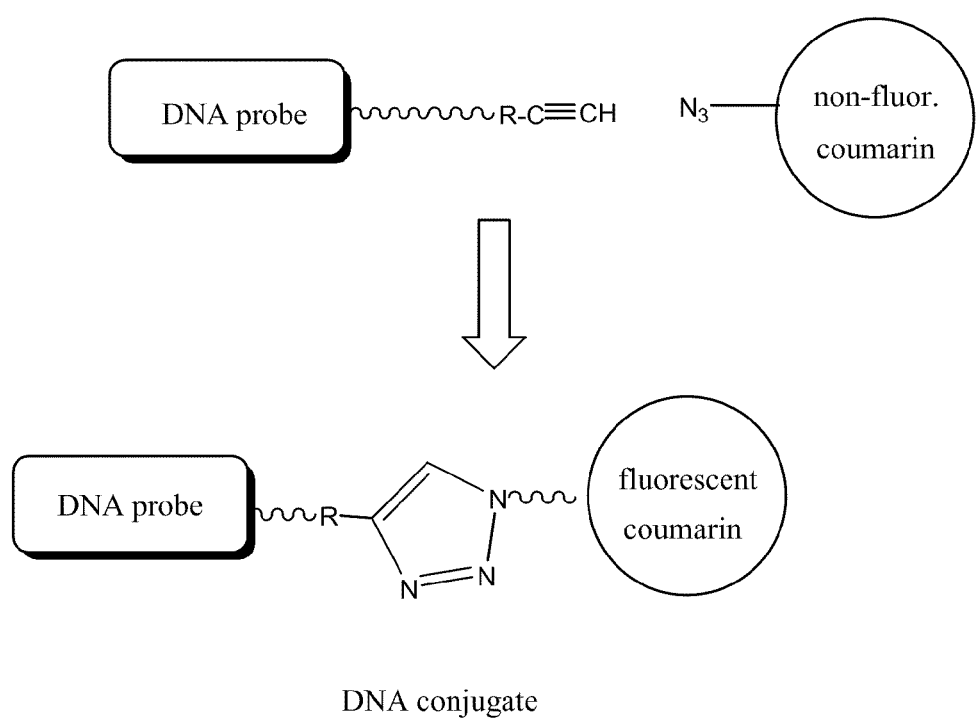
FIG. 5 illustrates formation of a fluorescent nucleotide conjugate formed form a non-fluorescent compound with an azide group.
Figure 6:
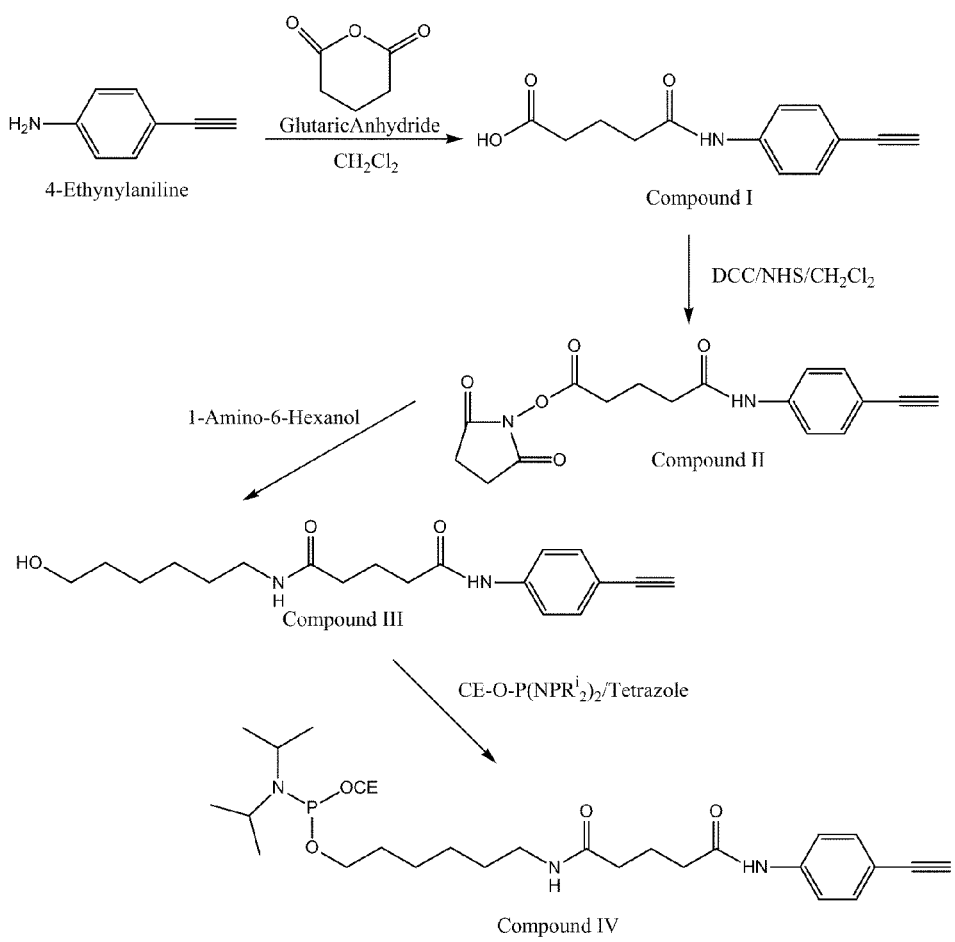
FIG. 6 shows a preferred synthetic method for making certain embodiments of the invention.
Figure 7:
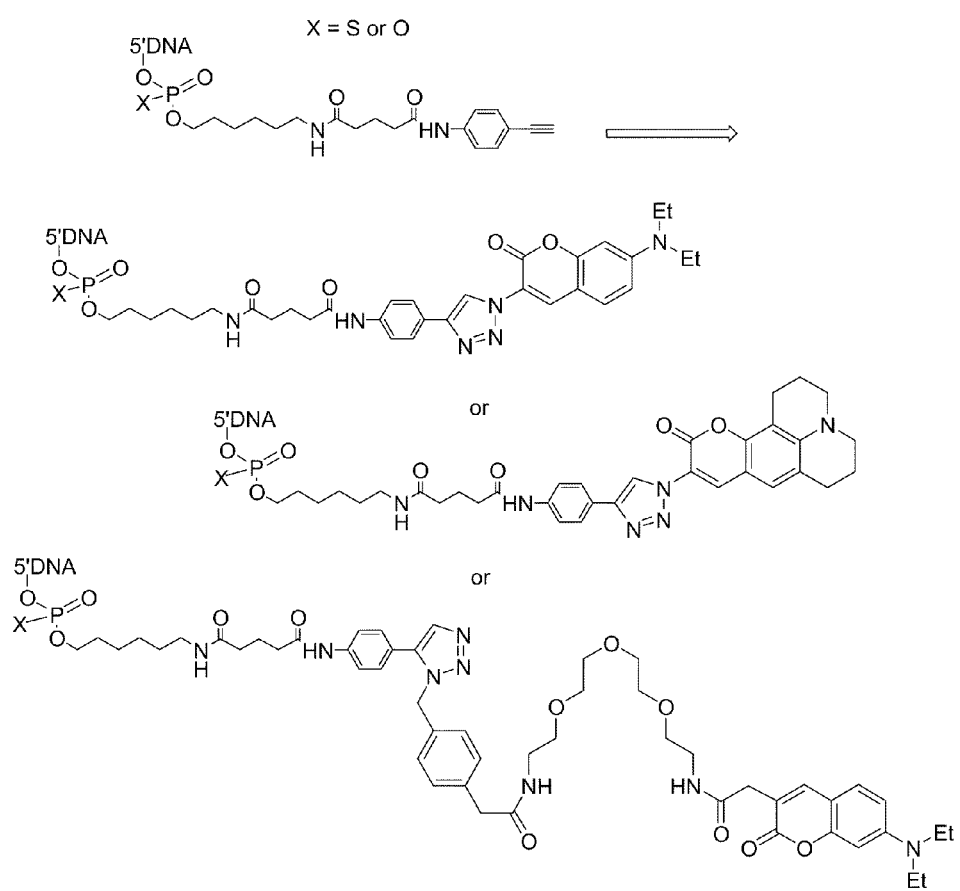
FIG. 7 shows the versatility of a preferred synthetic intermediate to make DNA conjugates.
Figure 8:
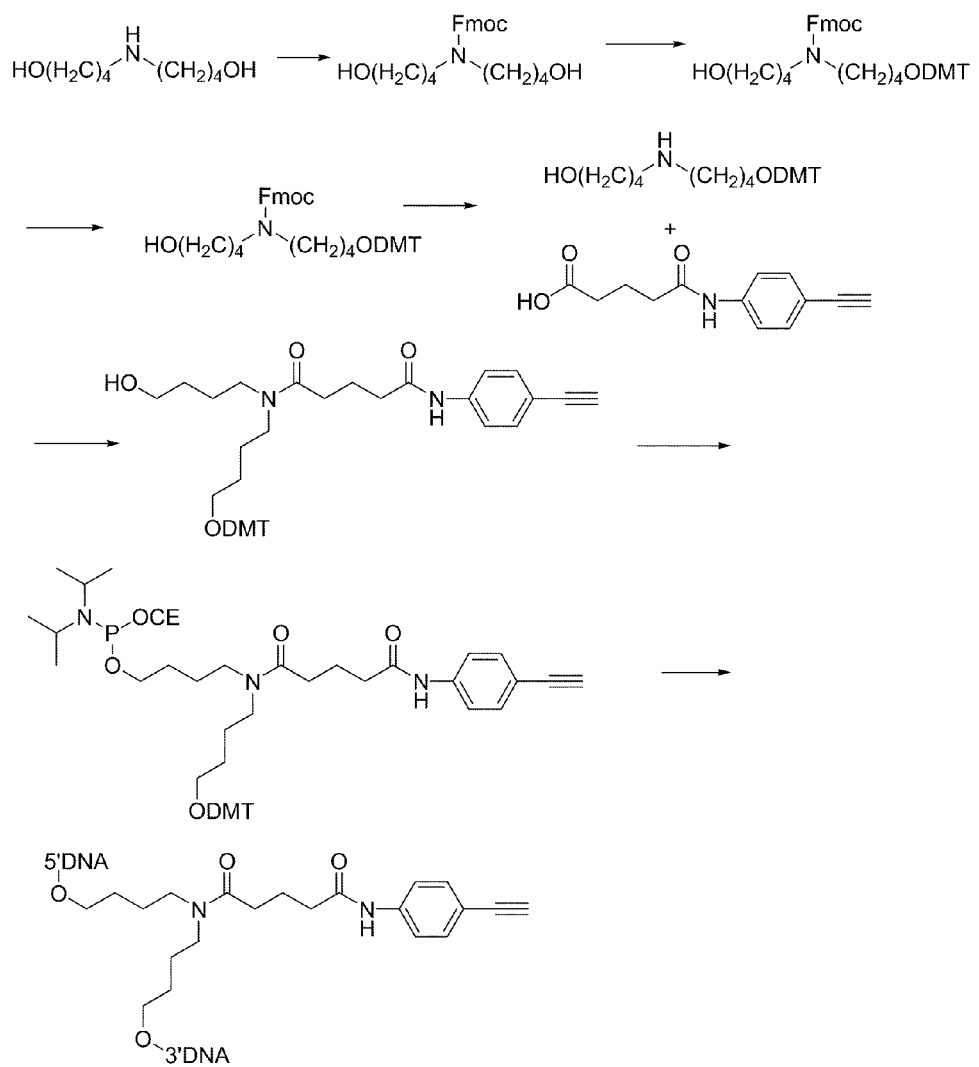
FIG. 8 show a preferred synthetic method for making certain embodiments of the invention.

The present invention relates to compositions useful as probes and in other applications and methods of their use. In some embodiments, nucleotides are prepared and functionalized with dyes. In some embodiments a first molecule is functionalized with an alkynyl group, a second molecule is functionalized with an azide group, and said first and second molecules are mixed under conditions to form a conjugate with a 1,2,3-triazol group. In further embodiments, a nucleotide is functionalized with an alkynyl group, a dye is functionalized with an azide group, and mixing the nucleotide and the dye forms a conjugate capable of emitting light or providing a detectable signal.

Conditions for coupling azide and alkynyl groups to form 1,2,3-triazols are disclosed in U.S. Patent Application, Pub. No. 20050032081, herein incorporated by reference in its entirety. A specific condition for azide/alkynyl coupling for a coumarin compound is disclosed in Wang, Org. Lett. 6:4603 (2004), herein incorporated by reference in its entirety.

There are a number of techniques that may be use for characterizing specific nucleic acid sequences that may employ the compositions and methods of the present invention. Examples of detection techniques include the "TaqMan" or nick-translation PCR assay described in U.S. Pat. No. 5,210,015 to Gelfand et al. (the disclosure of which is herein incorporated by reference), the assays described in U.S. Pat. Nos. 4,775,619 and 5,118,605 to Urdea (the disclosures of which are herein incorporated by reference), the catalytic hybridization amplification assay described in U.S. Pat. No. 5,403,711 to Walder and Walder (the disclosure of which is herein incorporated by reference), the cycling probe assay described in U.S. Pat. Nos. 4,876,187 and 5,011,769 to Duck et al., the target-catalyzed oligonucleotide modification assay described in U.S. Pat. Nos. 6,110,677 and 6,121,001 to Western et al. (the disclosures of which are herein incorporated by reference), the SNP detection methods of Orchid Bioscience in U.S. Pat. No. 5,952,174 (the disclosure of which is herein incorporated by reference), the methods of U.S. Pat. No. 5,882,867 to Ullman et al. (the disclosure of which is herein incorporated by reference) the polymerase chain reaction (PCR) described in U.S. Pat. Nos. 4,683,195, 4,683,202, and 4,965,188 to Mullis and Mullis et al. (the disclosures of which are herein incorporated by reference) and the ligase chain reaction (LCR) described in U.S. Pat. Nos. 5,427,930 and 5,494,810 to Birkenmeyer et al. and Barany et al. (the disclosures of which are herein incorporated by reference). The above examples are intended to be illustrative of nucleic acid-based detection assays and do not provide an exhaustive list. Each of these techniques requires a detection step for detecting a reaction product that is indicative of a desired target nucleic acid (e.g., detection of cleavage products, extension products, etc.). The present invention provides nucleotides, oligonucleotides (e.g., probes), and other nucleic acid molecule that find use in these and other detection-based technologies.

Another detection technology that uses oligonucleotides is the INVADER assay technology of Third Wave Technologies, Inc. (Madison, Wis.) (See e.g., U.S. Pat. Nos. 5,846,717, 5,985,557, 5,994,069, and 6,001,567 and PCT Publications WO 97/27214 and WO 98/42873, Lyamichev et al., Nat.

Biotech., 17:292 (1999), Hall et al., PNAS, USA, 97:8272 (2000), incorporated herein by reference in their entireties).

As used herein, "Aminoalkyl" means an alkyl having at least one hydrogen atom replaced with an amine group.

As used herein, "Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

As used herein, "Alkoxy" means an alkyl moiety attached through an oxygen bridge (e.g., —O-alkyl) such as methoxy, ethoxy, and the like.

As used herein, "Amine-oxo" group means a nitrogen atom covalently bound to a carbonyl group, or example an amide.

As used herein, "Aryl" means an aromatic moiety including both mono- and bicyclic ring systems such as, but not limited to, phenyl and naphthyl. It is intended that aryl includes aromatic heterocycles, i.e., carbocycle having at least one heteroatom selected from nitrogen, oxygen and sulfur. Representative aromatic heterocycles are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

As used herein, "Arylene" means a bridging aryl group.

As used herein, "Azide" means a chemical containing an azide group, $N_3$.

As used herein, "Biomolecule" means a molecule occurring in a living system or non-naturally occurring analogs thereof, including, for example, amino acids, peptides, oligopeptides, polypeptides, proteins, nucleotides, oligonucleotides, polynucleotides, nucleic acids, DNA, RNA, lipids, enzymes, receptors and receptor ligand-binding portions thereof.

As used herein, "Carbonyl" group means a carbon atom covalently bound by a double bond to oxygen.

As used herein, "CE" means a 2-cyanoethyl group.

As used herein, the terms "complementary" is used in reference to polynucleotides (i.e., a sequence of nucleotides such as an oligonucleotide or a target nucleic acid) related by the base-pairing rules. For example, for the sequence"5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

With regard to complementarity, it is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

In the context of certain embodiments, a "complex" means a conjugate formed by an association of atoms in a solution through non-covalent bonds and/or coordinate covalent bonds.

As used herein, "Conjugate" means a compound that has been formed by the joining of two or more compounds by covalent and/or non-covalent bonds.

As used herein, "DCC" means 1,3-dicyclohexylcarbodiimide.

As used herein, the term "dye" refers to a molecule, compound, or substance that can provide an optically detectable signal (e.g., fluorescent, colorimetric, etc). For example, dyes include fluorescent molecules that can be associated with nucleic acid molecules (e.g., Cy3).

As used herein, "DMT" is a dimethoxytrityl group.

As used herein, "EtOAc" means ethyl acetate.

As used herein, "Ethynyl" means a univalent group of —C≡CH.

The expression "essentially free" of a molecule means that the molecule is present in a composition only as an unavoidable impurity. It is to be understood that references herein to "impurities" are to be understood as to include unwanted reaction products that are not atomic isotopes or isomers formed during synthesis and also does not include residual solvents remaining from the process used in the preparation of the composition or excipients used in pharmaceutical preparations.

As used herein, "Ethynylaryl" means an ethynyl moiety attached through an aryl bridge, e.g., arylene.

As used herein, "Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

As used herein, "Hydroxyalkyl" means an alkyl having at least one hydrogen atom replaced with a hydroxy group.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contain a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxygenin; luminogenic, phosphorescent or fluorogenic moieties; mass tags; and fluorescent dyes alone or in combination with moieties that can suppress ("quench") or shift emission spectra by fluorescence resonance energy transfer (FRET). FRET is a distance-dependent interaction between the electronic excited states of two molecules (e.g., two dye molecules, or a dye molecule and a non-fluorescing quencher molecule) in which excitation is transferred from a donor molecule to an acceptor molecule without emission of a photon. (Stryer et al., 1978, Ann. Rev. Biochem., 47:819; Selvin, 1995, Methods Enzymol., 246:300, each incorporated herein by reference). As used herein, the term "donor" refers to a fluorophore that absorbs at a first wavelength and emits at a second, longer wavelength. The term "acceptor" refers to a moiety such as a fluorophore, chromophore, or quencher that has an absorption spectrum that overlaps the donor's emission spectrum, and that is able to absorb some or most of the emitted energy from the donor when it is near the donor group (typically between 1-100 nm). If the acceptor is a fluorophore, it generally then re-emits at a third, still longer wavelength; if it is a chromophore or quencher, it then releases the energy absorbed from the donor without emitting a photon. In some embodiments, changes in detectable emission from a donor dye (e.g. when an acceptor moiety is near or distant) are detected. In some embodiments, changes in detectable emission from an acceptor dye are detected. In preferred embodiments, the emission spectrum of the acceptor dye is distinct from the emission spectrum of the donor dye such that emissions from the dyes can be differentiated (e.g., spectrally resolved) from each other.

In some embodiments, a donor dye is used in combination with multiple acceptor moieties. In a preferred embodiment, a donor dye is used in combination with a non-fluorescing quencher and with an acceptor dye, such that when the donor dye is close to the quencher, its excitation is transferred to the quencher rather than the acceptor dye, and when the quencher is removed (e.g., by cleavage of a probe), donor dye excitation is transferred to an acceptor dye. In particularly preferred embodiments, emission from the acceptor dye is detected. See, e.g., Tyagi, et al., Nature Biotechnology 18:1191 (2000), which is incorporated herein by reference.

Labels may provide signals detectable by fluorescence (e.g., simple fluorescence, FRET, time-resolved fluorescence, fluorescence polarization, etc.), radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

In some embodiment a label comprises a particle for detection. In preferred embodiments, the particle is a phosphor particle. In particularly preferred embodiments, the phosphor particle is an up-converting phosphor particle (see, e.g., Ostermayer, F. W. Preparation and properties of infrared-to-visible conversion phosphors. Metall. Trans. 752, 747-755 [1971]). In some embodiments, rare earth-doped ceramic particles are used as phosphor particles. Phosphor particles may be detected by any suitable method, including but not limited to up-converting phosphor technology (UPT), in which up-converting phosphors transfer low energy infrared (IR) radiation to high-energy visible light. While the present invention is not limited to any particular mechanism, in some embodiments the UPT up-converts infrared light to visible light by multi-photon absorption and subsequent emission of dopant-dependant phosphorescence. See, e.g., U.S. Pat. No. 6,399,397, Issued Jun. 4, 2002 to Zarling, et al.; van De Rijke, et al., Nature Biotechnol. 19(3):273-6 [2001]; Corstjens, et al., IEE Proc. Nanobiotechnol. 152(2):64 [2005], each incorporated by reference herein in its entirety.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the terms "linking group" and "linker group" refer to an atom or molecule that links or bonds two entities (e.g., solid supports, oligonucleotides, or other molecules).

"Leaving group" means a molecular arraignment that creates higher relative reactivity by shifting electron density away from a reactive site causing nucleophiles to bond with the reactive site and break bonds with the leaving group. For example, the chlorine of an acid chloride shifts electron density away from the carbon of the carbonyl group increasing the carbonyl's carbon reactivity to alcohols that will form bonds between the oxygen the carbonyl's carbon and break the bond to the chlorine. There are many leaving groups known to those skilled in the art.

"Luminescence" means the light emitted by sources other than a hot, incandescent body. Luminescence includes chemiluminescence, fluorescence, and phosphorescence. Chemiluminescence is produced by certain chemical reactions. If the luminescence is caused by absorption of some form of radiant energy, then it is fluorescence, i.e., light of a visible color is emitted from a substance under stimulation or excitation by light or other forms of electromagnetic radiation or by certain other means. The light is given off only while the stimulation continues; in this the phenomenon differs from phosphorescence, in which light continues to be emitted after the excitation by other radiation has ceased. Methods for the detection of luminescence particularly fluorescence is described in a book by Mason, "fluorescent and luminescent probes for biological activity" $2^{nd}$ ed, 647 pages (1999).

As used herein, a "leaving group reagent" means a reagent used with the intent to introduce leaving groups into molecules.

As used herein, "NHS" means N-hydroxysuccinimide.

As used herein, the term "oligonucleotide" is defined as a molecule comprising two or more deoxyribonucleotides or ribonucleotides, preferably at least 5 nucleotides, more preferably at least about 10-15 nucleotides and more preferably at least about 15 to 30 nucleotides, although longer molecules are included within the scope. The exact size will depend on many factors, which in turn depend on the ultimate function or use of the oligonucleotide. The oligonucleotide may be generated in any manner, prior to or during a detection reaction, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

As used herein, "Nucleotide" means any of various compounds consisting of a nucleoside combined with a phosphate group and forming the basic constituent of DNA and RNA.

As used herein, the term "protecting group" refers to a molecule or chemical group that is covalently attached to a compound to prevent chemical modification of the compound or modification of specific chemical groups of the compound. For example, protecting groups may be attached to a reactive group of a compound to prevent the reactive group from participating in chemical reactions including, for example, intramolecular reactions. In some cases, a protecting group may act as a leaving group, such that when the molecule is added to another compound in a desired synthesis reaction, the protecting group is lost. The phosphoramidites of the present invention typically contain one or more protective groups prior to their addition to nucleic acid molecules. For example, the reactive phosphate of the phosphoramidite may contain one or more protecting groups. A detailed description of phosphoramidites and their addition to nucleic acid molecules is provided in Beaucage and Iyer, Tetrahedron 49:1925 (1993), herein incorporated by reference in its entirety.

The term "sample" as used herein is used in its broadest sense. A sample suspected of containing a nucleic acid molecule may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like. The term sample includes, but is not limited to, a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the terms "solid support" or "solid substrate" refer to any material that provides a solid or semi-solid structure with which another material can be attached. Such materials include smooth supports (e.g., metal, glass, plastic, silicon, carbon (e.g., diamond, graphite, nanotubes, fullerenes (e.g., C-60)) and ceramic surfaces) as well as textured and porous materials. Such materials also include, but are not limited to, gels, rubbers, polymers, and other non-rigid materials. Solid supports need not be composed of a single material. By way of example but not by way of limitation, a solid support may comprise a surface material (e.g. a layer or coating) and a different supporting material (e.g., gold-coated glass, diamond-coated metals and plastics, etc.) In some embodiments, solid supports comprise two or more different materials, e.g., in layers. Surface layers and coatings may be of any configuration and may partially or completely cover a supporting material. It is contemplated that solid supports may comprise any combination of layers, coatings, or other configurations of multiple materials. In some embodiments, a single material provides essentially all of the surface to which other material can be attached, while in other embodiments, multiple materials of the solid support are exposed for attachment of another material. Solid supports need not be flat. Supports include any type of shape including spherical shapes (e.g., beads). Materials attached to solid support may be attached to any portion of the solid support (e.g., may be attached to an interior portion of a porous solid support material). Preferred embodiments of the present invention have biological molecules such as nucleic acid molecules, charge tags, and proteins attached to solid supports. A biological material is "attached" to a solid support when it is associated with the solid support through a non-random chemical or physical interaction. In some preferred embodiments, the attachment is through a covalent bond. However, attachments need not be covalent or permanent. In some embodiments, materials are attached to a solid support through a "spacer molecule" or "linking group." Such spacer molecules are molecules that have a first portion that attaches to the biological material and a second portion that attaches to the solid support. Thus, when attached to the solid support, the spacer molecule separates the solid support and the biological materials, but is attached to both.

The term "substituted" as used herein means any of the above groups (e.g., alkyl, aryl, arylalkyl, heteroaryl, heteroarylalkyl, homocycle, heterocycle and/or heterocyclealkyl) wherein at least one hydrogen atom is replaced with a substituent. In the case of an oxo substituent ("=O"), two hydrogen atoms are replaced. When substituted, one or more of the above groups are "substituents." Substituents within the context of this invention include halogen, deuterium, tritium, borono, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle and heterocyclealkyl, as well as a saccharide, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. In addition, the above substituents may be further substituted with one or more of the above substituents, such that the substituent substituted alky, substituted aryl, substituted arylalkyl, substituted heterocycle or substituted heterocyclealkyl. R$_a$ and R$_b$ in this context may be the same or different and independently hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl. In the context of certain embodiments, a compound may be described as "unsubstituted" meaning that the compound does not contain extra substituents attached to the compound. For example, an unsubstituted amino acid refers to the chemical makeup of the amino acid without extra substituents, e.g., the amino acid does not contain carboxy terminal or amino terminal protecting group(s). For example, unsubstituted proline is the proline amino acid even though the amino group of proline may be considered disubstituted with alkyl groups.

As used herein, "TEA" means triethylamine.

As used herein, "TEAA" means Triethyl Ammonium Acetate.

In some embodiments, the invention relates to the generation of covalently linked conjugated biomolecules. These conjugates are formed under synthetic conditions that are sufficiently gentle to protect sensitive biomolecules such as dyes, nucleic acid molecules, proteins, and the like. Under appropriate conditions, if one molecule containing an azide (N$_3$) group is reacted with another containing an alkynyl group under appropriate conditions, a 1,2,3-triazol is formed, e.g., a 1,3-dipolar cycloaddition. Triazols are stable to aqueous and high temperature conditions.

In some embodiments, the invention provides DNA oligomer compositions comprising alkynyl-groups. Compositions containing phosphoramidite groups can be connected to the 5' or 3' end, or at an internal location, of a DNA oligomer. This molecule can then be reacted with azide-containing molecules to form a detectable conjugate. In preferred embodiments, the conjugate is formed by the coupling DNA to dye molecules and/or "solid-supports" used in an array. In another embodiment, the invention relates to DNA-Dye conjugate synthesis. In further embodiments, a fluorochrome is produced from two non-fluorescent starting reactants. In further embodiments, the fluorochrome is a conjugate with DNA oligomers.

It is not intended to limit current embodiments of the invention to any particular dye. The methods disclosed herein can be appropriately adapted to any number of know dyes that are or may be chemically functionalized with an azide group. It is preferred, that the azide group is substituted on an aromatic portion of the chemical structure of the dye. In addition it is preferred that the fluorescence range of the dye changes so that reaction with an ethynyl groups to form a 1,2,3-triazol provides a detectable difference in emitted light. Embodiments of fluorescent coumarin are preferred because they fluoresce in the range of 400-470 nm (the "blue" range). One reason this is preferred is because mutiplex applications with other fluorochromes exhibiting fluorescence at other wavelengths. Azide functionalized of dyes include, without limitation, those with the following chemical structures: xanthene dyes, carbocyanine dyes, polymethine dyes including Astra Violet FR, thiofalvine T, psuedoisocyanine, oxacarbocyanine dyes, acridine dyes, azine dyes, diphenylmethane dyes, methine dyes, oxazine dyes, cyanine dyes, and styryl dyes such as benzothiophenone, 14H-anthra{2.1.9-MNA} thioxanthen-14-one, 2(3oxobenzothien2(3H)yliden) benzothiophenone, anthraquinone 1,4-bis(2,6-diethyl-4-methlphen1) aminoanthracendione, 3,9-perylendicarboxlic acid, bis-2-methylpropyl ester, among others. See, for example, the metachromatic dyes noted in Urban et al., 2000 *Acta. Histochem.* 102:259-272. Still other dyes that are useful include the nonyl Acridine Orange dye (3,6-Bis-(dimethylamino)-10-nonylacridinium bromide, Molecular Probes, Eugene, Oreg.); the Acridine Red™ dye (also commercially available as Pyronin B, Sigma-Aldrich Corp., St. Louis, Mo.), the Toluidine Blue dye (2-amino-7-dimethylamino-3-methylphenothiazinium chloride, Sigma-Aldrich Corp., St. Louis, Mo.), hydrosystilbamidine (Molecular Probes, Eugene, Oreg.) and cyanine dyes including the SYTO™ dyes (Molecular Probes, Eugene, Oreg.), the TOTO™ dyes (Molecular Probes, Eugene, Oreg.), the YOYO™ dyes (Molecular Probes, Eugene, Oreg.), the BOBO™ dyes (Molecular Probes, Eugene, Oreg.), the Neutral Red™ dye (3-amino-7-dimethylamino-2-methylphenazine hydrochloride, Sigma-Aldrich Corp., St. Louis, Mo.), the Basic Orange™ 21 dye (Sigma-Aldrich Corp., St. Louis, Mo.), the DiOC dye (1,1'-dimethyloxacarbocyanine, Molecular Probes, Eugene, Oreg.), the Pyronin™ Y dye (Polysciences, Inc., Warrington, Pa.), the Methylene Blue™ dye (3-bis-(dimethylamino)-phenothiazin-5-ium chloride, Molecular Probes, Eugene, Oreg.), the Auramine™ O dye (4,4'-(imidocarbonyl)-bis-(N,N,-dimethylaniline) monohydrochloride, Sigma-Aldrich Corp., St. Louis, Mo.), the LDS™ 751 dye (quinolinium, 6-(dimethylamino)-2-[4-[4-(dimethylamino)phenyl]-1,3-butadienyl]-2-ethyl perchlorate, Molecular Probes, Eugene, Oreg.), the Red series dyes, ethidium bromide (Sigma-Aldrich Corp., St. Louis, Mo.), propidium iodide (3,8-Diamino-5-(3-diethylaminopropyl)-6-phenyl-phenanthridinium iodide methiodide, Sigma-Aldrich Corp., St. Louis, Mo.), hexidium iodide (Molecular Probes, Eugene, Oreg.), dihydroethidium (Molecular Probes, Eugene, Oreg.), ethidium monoazide (Molecular Probes, Eugene, Oreg.), the Thiazole Orange™ dye (Becton Dickinson, Franklin Lakes, N.J.), among others, and combinations thereof.

Solid substrates that are useful in practicing the present invention (e.g., for constructing the devices of the present invention) can be made of practically any physicochemically stable material. The substrates can be either rigid or flexible and can be either optically transparent or optically opaque. The substrates can be electrical insulators, conductors or semiconductors. Further, the substrates can be substantially impermeable to liquids, vapors and/or gases or, alternatively, the substrates can be permeable to one or more of these classes of materials. Exemplary substrate materials include, but are not limited to, inorganic crystals, inorganic glasses, inorganic oxides, metals, organic polymers and combinations thereof. In some embodiments, the substrates have microchannels therein for the delivery of sample and/or other reagents to the substrate surface or detection regions thereon. The design and use of microchannels are described, for example, in U.S. Pat. Nos. 6,425,972, 6,418,968, 6,447,727, 6,432,720, 5,976,336, 5,882,465, 5,876,675, 6,186,660, 6,100,541, 6,379,974, 6,267,858, 6,251,343, 6,238,538, 6,182,733, 6,068,752, 6,429,025, 6,413,782, 6,274,089, 6,150,180, 6,046,056, 6,358,387, 6,321,791, 6,326,083, 6,171,067, and 6,167,910, all of which are incorporated herein by reference.

In some embodiments of the present invention, inorganic crystals and inorganic glasses are utilized as substrate materials (e.g., LiF, NaF, NaCl, KBr, KI, $CaF_2$, $MgF_2$, $HgF_2$, BN, $AsS_3$, ZnS, $Si_3N_4$ and the like). The crystals and glasses can be prepared by art standard techniques (See, e.g., Goodman, C. H. L., *Crystal Growth Theory and Techniques*, Plenum Press, New York 1974). Alternatively, the crystals can be purchased commercially (e.g., Fischer Scientific). The crystals can be the sole component of the substrate or they can be coated with one or more additional substrate components. Thus, it is within the scope of the present invention to utilize crystals coated with, for example one or more metal films or a metal film and an organic polymer. Additionally, a crystal can constitute a portion of a substrate which contacts another portion of the substrate made of a different material, or a different physical form (e.g., a glass) of the same material. Other useful substrate configurations utilizing inorganic crystals and/or glasses will be apparent to those of skill in the art.

In other embodiments of the present invention, inorganic oxides are utilized as the substrate. Inorganic oxides of use in the present invention include, for example, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $SnO_2$, $PbO_2$ and the like. The inorganic oxides can be utilized in a variety of physical forms such as films, supported powders, glasses, crystals and the like. A substrate can consist of a single inorganic oxide or a composite of more than one inorganic oxide. For example, a composite of inorganic oxides can have a layered structure (i.e., a second oxide deposited on a first oxide) or two or more oxides can be arranged in a contiguous non-layered structure. In addition, one or more oxides can be admixed as particles of various sizes and deposited on a support such as a glass or metal sheet. Further, a layer of one or more inorganic oxides can be intercalated between two other substrate layers (e.g., metal-oxide-metal, metal-oxide-crystal).

In some embodiments, the substrate is a rigid structure that is impermeable to liquids and gases. In this embodiment, the substrate consists of a glass plate onto which a metal, such as gold is layered by evaporative deposition. In a still further embodiment, the substrate is a glass plate ($SiO_2$) onto which a first metal layer such as titanium has been layered. A layer of a second metal such as gold is then layered on top of the first metal layer.

In still further embodiments of the present invention, metals are utilized as substrates. The metal can be used as a crystal, a sheet or a powder. The metal can be deposited onto a backing by any method known to those of skill in the art including, but not limited to, evaporative deposition, sputtering, electroless deposition, electrolytic deposition and adsorption or deposition of preformed particles of the metal including metallic nanoparticles.

Metal preferred as substrates include, but are not limited to, gold, silver, platinum, palladium, nickel and copper. In one embodiment, more than one metal is used. The more than one metal can be present as an alloy or they can be formed into a layered "sandwich" structure, or they can be laterally adjacent to one another. In a preferred embodiment, the metal used for the substrate is gold. In a particularly preferred embodiment the metal used is gold layered on titanium.

In still other embodiments of the present invention, organic polymers are utilized as substrate materials. Organic polymers useful as substrates in the present invention include polymers that are permeable to gases, liquids and molecules in solution. Other useful polymers are those that are impermeable to one or more of these same classes of compounds.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers and phenolic resins (See, Cognard, J. ALIGNMENT OF NEMATIC LIQUID CRYSTALS AND THEIR MIXTURES, in Mol. Cryst. Liq. Cryst. 1:1-74 (1982)). Presently preferred organic polymers include polydimethylsiloxane, polyethylene, polyacrylonitrile, cellulosic materials, polycarbonates and polyvinyl pyridinium.

In a presently preferred embodiment, the substrate is permeable and it consists of a layer of gold, or gold over titanium, which is deposited on a polymeric membrane, or other material, that is permeable to liquids, vapors and/or gases. The liquids and gases can be pure compounds (e.g., chloroform, carbon monoxide) or they can be compounds that are dispersed in other molecules (e.g., aqueous protein solutions, herbicides in air, alcoholic solutions of small organic molecules). Useful permeable membranes include, but are not limited to, flexible cellulosic materials (e.g., regenerated cellulose dialysis membranes), rigid cellulosic materials (e.g., cellulose ester dialysis membranes), rigid polyvinylidene fluoride membranes, polydimethylsiloxane and track etched polycarbonate membranes.

In those embodiments wherein the permeability of the substrate is not a concern and a layer of a metal film is used, the film can be as thick as is necessary for a particular application. For example, if the film is used as an electrode, the film can be thicker than in an embodiment in which it is necessary for the film to be transparent or semi-transparent to light.

Thus, in a preferred embodiment, the film is of a thickness of from about 0.01 nanometer to about 1 micrometer. In a further preferred embodiment, the film is of a thickness of from about 5 nanometers to about 100 nanometers. In yet a further preferred embodiment, the film is of a thickness of from about 10 nanometers to about 50 nanometers.

In some embodiments, the surface of the substrate is functionalized so that a recognition moiety is immobilized on the surface of the substrate. In some embodiments, the immobilized recognition moiety forms a detection region. In some embodiments, a plurality of detection regions are formed on the surface of the substrate. In some embodiments, the same recognition moiety is provided on two or more of the plurality of detection regions, while in other embodiments, at least two different recognition moieties are immobilized on one or more of the plurality of detection regions. In some embodiments, the recognition moieties are arrayed in discreet detection regions on the substrate surfaces by the methods described in more detail below.

In some embodiments, the surface of the substrate is first functionalized by forming a self-assembled monolayer (SAM) on the substrate surface. Self-assembled monolayers are preferably depicted as an assembly of organized, closely packed linear molecules. There are two widely-used methods to deposit molecular monolayers on solid substrates: Langmuir-Blodgett transfer and self-assembly. Additional methods include techniques such as depositing a vapor of the monolayer precursor onto a substrate surface and the layer-by-layer deposition of polymers and polyelectrolytes from solution (Ladam et al., Protein Adsorption onto Auto-Assembled Polyelectrolyte Films, Langmuir; 2001; 17(3); 878-882).

The composition of a layer of a SAM useful in the present invention can be varied over a wide range of compound structures and molar ratios. In one embodiment, the SAM is formed from only one compound. In a presently preferred embodiment, the SAM is formed from two or more components. In another preferred embodiment, when two or more components are used, one component is a long-chain hydrocarbon having a chain length of between 10 and 25 carbons and a second component is a short-chain hydrocarbon having a chain length of between 1 and 9 carbon atoms. In particularly preferred embodiments, the SAM is formed from $CH_3(CH_2)_{15}SH$ and $CH_3(CH_2)_4SH$ or $CH_3(CH_2)_{15}SH$ and $CH_3(CH_2)_9SH$. In any of the above described embodiments, the carbon chains can be functionalized at the w-terminus (e.g., $NH_2$, COOH, OH, CN), at internal positions of the chain (e.g., aza, oxa, thia) or at both the ω-terminus and internal positions of the chain.

A recognition moiety can be attached to the surface of a SAM by any of a large number of art-known attachment methods. In one preferred embodiment, a reactive SAM component is attached to the substrate and the recognition moiety is subsequently bound to the SAM component via the reactive group on the component and a group of complementary reactivity on the recognition moiety (See, e.g., Hegner et al. Biophys. J. 70:2052-2066 (1996)). In another preferred embodiment, the recognition moiety is attached to the SAM component prior to immobilizing the SAM component on the substrate surface: the recognition moiety-SAM component cassette is then attached to the substrate. In a still further preferred embodiment, the recognition moiety is attached to the substrate via a displacement reaction. In this embodiment, the SAM is preformed and then a fraction of the SAM components are displaced by a recognition moiety or a SAM component bearing a virus recognition moiety. In still other embodiments, the polypeptide recognition moieties are adsorbed directly onto hydrophobic monolayers such as $CH_3(CH_2)_{15}SH$. In embodiments where the recognition moiety is an antibody or other molecule that binds to protein A, protein A is first attached to the monolayer followed by the antibody, which is bound by protein A.

The discussion that follows focuses on the attachment of a reactive SAM component to the substrate surface. This focus is for convenience only and one of skill in the art will understand that the discussion is equally applicable to embodiments in which the SAM component-recognition moiety is preformed prior to its attachment to the substrate. As used herein, "reactive SAM components" refers to components that have a functional group available for reaction with a recognition moiety or other species following the attachment of the component to the substrate.

Currently favored classes of reactions available with reactive SAM components are those that proceed under relatively mild conditions. These include, but are not limited to nucleophilic substitutions (e.g., reactions of amines and alcohols with acyl halides), electrophilic substitutions (e.g., enamine reactions) and additions to carbon-carbon and carbon-heteroatom multiple bonds (e.g., Michael reaction, Diels-Alder addition). These and other useful reactions are discussed in March, ADVANCED ORGANIC CHEMISTRY, Third Ed., John Wiley & Sons, New York, 1985.

According to the present invention, a substrate's surface is functionalized with SAM, components and other species by covalently binding a reactive SAM component to the substrate surface in such a way as to derivatize the substrate surface with a plurality of available reactive functional groups. Azides are preferred reactive groups. Reactive groups which can be used in practicing the present invention also include, for example, amines, hydroxyl groups, carboxylic acids, carboxylic acid derivatives, alkenes, sulfhydryls, siloxanes, etc.

A wide variety of reaction types are available for the functionalization of a substrate surface. For example, substrates constructed of a plastic such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized substrates can be made from etched, reduced polytetrafluoroethylene.

When the substrates are constructed of a siliaceous material such as glass, the surface can be derivatized by reacting the surface Si—OH, SiO-H, and/or Si—Si groups with a functionalizing reagent. When the substrate is made of a metal film, the surface can be derivatized with a material displaying avidity for that metal.

In a preferred embodiment, wherein the substrates are made from glass, the covalent bonding of the reactive group to the glass surface is achieved by conversion of groups on the substrate's surface by a silicon modifying reagent such as:

$(RO)_3$—Si—$R^1$—$X^1$     (1)

where R is an alkyl group, such as methyl or ethyl, $R^1$ is a linking group between silicon and X and X is a reactive group or a protected reactive group. The reactive group can also be a recognition moiety as discussed below. Silane derivatives having halogens or other leaving groups beside the displayed alkoxy groups are also useful in the present invention.

A number of siloxane functionalizing reagents can be used, for example:
1. Hydroxyalkyl siloxanes (Silylate surface, functionalize with diborane, and $H_2O_2$ to oxidize the alcohol)
   a. allyl trichlorosilane→→3-hydroxypropyl
   b. 7-oct-1-enyl trichlorosilane→→8-hydroxyoctyl
2. Diol (dihydroxyalkyl) siloxanes (silylate surface and hydrolyze to diol)
   a. (glycidyl trimethoxysilane→→(2,3-dihydroxypropyloxy)propyl
3. Aminoalkyl siloxanes (amines requiring no intermediate functionalizing step).
   a. 3-aminopropyl trimethoxysilane→aminopropyl
4. Dimeric secondary aminoalkyl siloxanes
   a. bis(3-trimethoxysilylpropyl)amine→bis(silyloxylpropyl)amine.

It will be apparent to those of skill in the art that an array of similarly useful functionalizing chemistries are available when SAM components other than siloxanes are used. Thus, for example similarly functionalized alkyl thiols can be attached to metal films and subsequently reacted to produce the functional groups such as those exemplified above.

In another preferred embodiment, the substrate is at least partially a metal film, such as a gold film, and the reactive group is tethered to the metal surface by an agent displaying avidity for that surface. In a presently preferred embodiment, the substrate is at least partially a gold film and the group which reacts with the metal surface comprises a thiol, sulfide or disulfide such as:

Y—S—$R^2$—$X^2$     (2)

$R^2$ is a linking group between sulfur and $X^2$ and $X^2$ is an azide or azide dye. $X^2$ can also be a recognition moiety as discussed below. Y is a member selected from the group consisting of H, $R^3$ and $R^3$—S—, wherein $R^2$ and $R^3$ are independently selected. When $R^2$ and $R^3$ are the same, symmetrical sulfides and disulfides result, and when they are different, asymmetrical sulfides and disulfides result.

A large number of functionalized thiols, sulfides and disulfides are commercially available (Aldrich Chemical Co., St. Louis). Additionally, those of skill in the art have available to them a manifold of synthetic routes with which to produce additional such molecules. For example, amine-functionalized thiols can be produced from the corresponding halo-amines, halo-carboxylic acids, etc. by reaction of these halo precursors with sodium sulfhydride. See, e.g., Reid, ORGANIC CHEMISTRY of BIVALENT SULFUR, VOL 1, pp. 21-29, 32-35, vol. 5, pp. 27-34, Chemical Publishing Co., New York, 1.958, 1963. Additionally, functionalized sulfides can be prepared via alkylthio-de-halogenation with a mercaptan salt (See, Reid, ORGANIC CHEMISTRY OF BIVALENT SULFUR, vol. 2, pp. 16-21, 24-29, vol. 3, pp. 11-14, Chemical Publishing Co., New York, 1960). Other methods for producing compounds useful in practicing the present invention will be apparent to those of skill in the art.

In another preferred embodiment, the functionalizing reagent provides for more than one reactive group per each reagent molecule. Using reagents such as Compound 3, below, each reactive site on the substrate surface is, in essence, "amplified" to two or more functional groups:

$(RO)_3$—Si—$R^2$—$(X^2)_n$     (3)

where R is an alkyl group, such as methyl, $R^2$ is a linking group between silicon and $X^2$, $X^2$ is a azide or azide dye, reactive group or a protected reactive group and n is an integer between 2 and 50, and more preferably between 2 and 20.

Similar amplifying molecules are also of use in those embodiments wherein the substrate is at least partially a metal film. In these embodiments the group which reacts with the metal surface comprises a thiol, sulfide or disulfide such as in Formula (4):

Y—S—$R^2$—$(X^2)_n$     (4)

As discussed above, $R^2$ is a linking group between sulfur and $X^2$ and $X^2$ is an azide, azide dye, reactive group or a protected reactive group. $X^2$ can also be a recognition moiety. Y is a member selected from the group consisting of H, $R^3$ and $R^3$—S—, wherein $R^2$ and $R^3$ are independently selected.

R groups of use for $R^1$, $R^2$ and $R^3$ in the above described embodiments of the present invention include, but are not limited to, alkyl, substituted alkyl, aryl, arylalkyl, substituted aryl, substituted arylalkyl, acyl, halogen, hydroxy, amino, alkylamino, acylamino, alkoxy, acyloxy, aryloxy, aryloxyalkyl, mercapto, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups.

In each of Formulae 1-4, above, each of $R^1$, $R^2$ and $R^3$ are either stable or they can be cleaved by chemical or photochemical reactions. For example, R groups comprising ester or disulfide bonds can be cleaved by hydrolysis and reduction, respectively. Also within the scope of the present invention is the use of R groups which are cleaved by light such as, for example, nitrobenzyl derivatives, phenacyl groups, benzoin esters, etc. Other such cleaveable groups are well-known to those of skill in the art.

In another preferred embodiment, the organosulfur compound is partially or entirely halogenated. An example of compounds useful in this embodiment include:

$X^1Q_2C(CQ^1_2)_mZ^1(CQ^2_2)_nSH$     (5)

wherein, $X^1$ is a member selected from the group consisting of H, azide, azide dye, halogen reactive groups and protected reactive groups. Reactive groups can also be recognition moieties as discussed below. Q, $Q^1$ and $Q^2$ are independently members selected from the group consisting of H and halogen. $Z^1$ is a member selected from the group consisting of —$CQ_2$-, —$CQ^1_2$-, —$CQ^2_2$-, —O—, —S—, $NR^4$—, —C(O)$NR^4$ and $R^4NC(OO$—, in which $R^4$ is a member selected from the group consisting of H, alkyl, substituted alkyl, aryl, substituted aryl, heteroaryl and heterocyclic groups and m and n are independently a number between 0 and 40.

The reactive functional groups ($X^1$ and $X^2$) are, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) azide group or azide substituted dyes which are capable of participating in a 1,3-dipolar cycloaddition with an alkynyl group to form, a 1,2,3-triazol.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups which can be converted to disulfides or reacted with acyl halides;

(h) amine or sulfhydryl groups which can be, for example, acylated or alkylated;

(i) alkenes which can undergo, for example, cycloadditions, acylation, Michael addition, etc;

(j) epoxides which can react with, for example, amines and hydroxyl compounds; and The reactive functional groups can be chosen such that they do not participate in, or interfere with, the reaction controlling the attachment of the functionalized SAM component onto the substrate's surface. Alternatively, the reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

In a preferred embodiment, the SAM component bearing the recognition moiety is attached directly and essentially irreversibly via a "stable bond" to the surface of the substrate. A "stable bond", as used herein, is a bond which maintains its chemical integrity over a wide range of conditions (e.g., amide, carbamate, carbon-carbon, ether, etc.). In another preferred embodiment, the SAM component bearing the recognition moiety is attached to the substrate surface by a "cleaveable bond". A "cleaveable bond", as used herein, is a bond that is designed to undergo scission under conditions which do not degrade other bonds in the recognition moiety-analyte complex. Cleaveable bonds include, but are not limited to, disulfide, imine, carbonate and ester bonds.

In certain embodiments, it is advantageous to have the recognition moiety attached to a SAM component having a structure that is different than that of the constituents of the bulk SAM. In this embodiment, the group to which the recognition moiety is bound is referred to as a "spacer arm" or "spacer." Using such spacer arms, the properties of the SAM adjacent to the recognition moiety can be controlled. Properties that are usefully controlled include, for example, hydrophobicity, hydrophilicity, surface-activity and the distance of the recognition moiety from the plane of the substrate and/or the SAM. For example, in a SAM composed of alkanethiols, the recognition moiety can be attached to the substrate or the surface of the SAM via an amine terminated poly(ethyleneglycol). Numerous other combinations of spacer arms and SAMs are accessible to those of skill in the art.

The hydrophilicity of the substrate surface can be enhanced by reaction with polar molecules such as amine-, hydroxyl- and polyhydroxylcontaining molecules. Representative examples include, but are not limited to, polylysine, polyethyleneimine, poly(ethyleneglycol) and poly(propyleneglycol). Suitable functionalization chemistries and strategies for these compounds are known in the art (See, for example, Dunn, R. L., et al., Eds. POLYMERIC DRUGS AND DRUG DELIVERY SYSTEMS, ACS Symposium Series Vol. 469, American Chemical Society, Washington, D.C. 1991).

The hydrophobicity of the substrate surface can be modulated by using a hydrophobic spacer arm such as, for example, long chain diamines, long chain thiols, a, w-amino acids, etc. Representative hydrophobic spacers include, but are not limited to, 1,6-hexanediamine, 1,8-octanediamine, 6-aminohexanoic acid and 8-aminooctanoic acid.

The substrate surface can also be made surface-active by attaching to the substrate surface a spacer that has surfactant properties. Compounds useful for this purpose include, for example, aminated or hydroxylated detergent molecules such as, for example, 1-aminododecanoic acid.

In another embodiment, the spacer serves to distance the virus recognition moiety from the substrate or SAM. Spacers with this characteristic have several uses. For example, a recognition moiety held too closely to the substrate or SAM surface may not react with incoming analyte, or it may react unacceptably slowly. When an analyte is itself sterically demanding, the reaction leading to recognition moiety-analyte complex formation can be undesirably slowed, or not occur at all, due to the monolithic substrate hindering the approach of the two components.

In some embodiments where the recognition moiety is a polynucleotide or polypeptide, a plurality of recognition moieties are arrayed on the substrates using photo activated chemistry, microcontact printing, and ink-jet printing. In particularly preferred embodiments, photolithography is utilized (See e.g., U.S. Pat. Nos. 6,045,996; 5,925,525; and 5,858,659; each of which is herein incorporated by reference). Using a series of photolithographic masks to define substrate exposure sites, followed by specific chemical synthesis steps, the process constructs high-density arrays of oligonucleotides, with each probe in a predefined position in the array. Multiple probe arrays are synthesized simultaneously on, for example, a large glass wafer. The wafers are then diced, and individual probe arrays are packaged in injection-molded plastic cartridges, which protect them from the environment and serve as chambers for hybridization.

In other embodiments, nucleic acid recognition moieties are electronically captured on a suitable substrate (See e.g., U.S. Pat. Nos. 6,017,696; 6,068,818; and 6,051,380; each of which are herein incorporated by reference). Through the use of microelectronics, this technology enables the active movement and concentration of charged molecules to and from designated test sites on its semiconductor microchip. DNA capture probes unique to a given target are electronically placed at, or "addressed" to, specific sites on the microchip. Since DNA has a strong negative charge, it can be electronically moved to an area of positive charge.

In still further embodiments, recognition moieties are arrayed on a suitable substrate by utilizing differences in surface tension (See e.g., U.S. Pat. Nos. 6,001,311; 5,985, 551; and 5,474,796; each of which is herein incorporated by reference). This technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning In still further embodiments, recognition moieties are spotted onto a suitable substrate. Such spotting can be done by hand with a capillary tube or micropipette, or by an automated spotting apparatus such as those available from Affymetrix and Gilson (See e.g., U.S. Pat. Nos. 5,601,980; 6,242,266; 6,040,193; and 5,700,637; each of which is incorporated herein by reference).

In some embodiments, following immobilization of the recognition moiety on the surface of the substrate, the remainder of the substrate is blocked to guard against non-specific binding to the substrate surface. Examples of suitable blocking agents, include, but are not limited to, serum albumins, zwitterionic polymers, adsorbed lipid layers, dextran and other sugars, cross-linked lipids, polyethylene oxide, polyoxazolines, hydrogels, and milk. In preferred embodiments, the blocking agent bovine serum albumin, human serum albumin or equine serum albumin.

In some embodiments of the present invention, variant sequences are detected using a DNA chip hybridization assay. In this assay, a series of oligonucleotide probes are affixed to a solid support. The oligonucleotide probes are designed to be unique to a given SNP or mutation. The DNA sample of interest is contacted with the DNA "chip" and hybridization is detected.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

EXAMPLES

The following examples are provided in order to demonstrate and further illustrate certain preferred embodiments and aspects of the present invention and are not to be construed as limiting the scope thereof.

Example 1

DNA Synthesis

The DNA synthesis cycle typically begins with the 3'-hydroxyl nucleoside attached to a solid Controlled-Pore Glass (CPG) support through a long spacer arm. This support allows excess reagents to be removed by filtration and eliminates the need for purification steps between base additions.

The first step in the synthesis is the removal of the dimethoxytrityl (DMT) group with TCA to free the 5'-hydroxyl for the coupling reaction. The next step, activation, is achieved by simultaneously adding a phosphoramidite derivative of the next nucleotide and tetrazole, a weak acid to the reaction chamber. The tetrazole protonates the nitrogen of the phosphoramidite, making it susceptible to nucliophilic attack. This intermediate is very reactive and the following coupling step is complete in less than 30 seconds. The 5'-OH group of the phosphoramidite is blocked with the DMT group.

The capping step terminates any chains that did not undergo coupling. The unreacted chain has a free 5'-OH which can be terminated or capped by acetylation to become "failure products". This is achieved with acetic anhydride and 1-methylimidazole. The DMT group of the successful coupling step protects the 5'-OH end from being capped. Although this step is not absolutely necessary for DNA synthesis, it minimizes the length of impurities and thus facilitates trityl-on HPLC Purification.

The internucleotide linkage is then converted from the less stable phosphite to the phosphotriester in the oxidation step. Iodine may be used as the oxidizing agent and water as the oxygen donor. (For phosphorothioate oligonucleotides, the internucleotide phosphite is sulfurized between coupling and capping).

After oxidation, the DMT group may be removed with trichloroacetic acid and the cycle is repeated until chain elongation is complete. The oligo is then cleaved from the solid support with concentrated ammonium hydroxide. Ammonia treatment also removes the cyanoethyl phosphate protecting groups. The crude DNA in ammonium hydroxide solution may then be heated at 65 degrees for 1 hour to remove the protecting groups on the exocyclic amines of the base.

Example 2

Synthesis of Propargyl Phosphoramidite 5-(4-ethynylphenyl)amino-5-oxo-pentanoic acid: To a solution of 4-ethynylaniline (0.99 g, 8.5 mmol) in $CH_2Cl_2$ (100 ml) is added glutaric anhydride (1.06 g, 9.30 mmol). After 1 h, the resulting slurry is concentrated by rotary evaporation and the crude mixture is purified by silica column chromatography (10% methanol/5% $TEA/CH_2Cl_2$).

(2,5-dioxopyrrolidin-1-yl) 5-(4-ethynylphenyl)amino-5-oxo-pentanate: NHS (0.14 g, 1.2 mmol) and DCC (0.30 g, 1.5 mmol) is added to a stirred solution of 5-(4-ethynylphenyl) amino-5-oxo-pentanoic acid (0.26 g, 1.2 mmol) in $CH_2Cl_2$ (50 ml). After 2 h, the slurry is filtered to remove any precipitated DCU and the filtrate is concentrated by rotary evaporation. The residue is purified by silica column chromatography (EtOAc).

N'-(6-hydroxyhexyl)-N-(4-ethynylphenyl)-pentandiamide: A solution of (2,5-dioxopyrrolidin-1-yl) 5-(4-ethynylphenyl)amino-5-oxo-pentanate (0.2 g, 0.6 mmol) in CH$_2$Cl$_2$ (10 ml) is added slowly to a solution of 1-amino-6-hexanol (0.35 g, 3.0 mmol) in CH$_2$Cl$_2$ (50 ml) with vigorous stirring. The crude reaction solution is concentrated by rotary evaporation and the mixture is purified by silica column chromatography (10% methanol/5% TEA/CH$_2$Cl$_2$).

N'-(6-aminohexyl 2-cyanoethyl dosopropylamidophosphite)-N-(4-ethynylphenyl)-pentandiamide: Compound N'-(6-hydroxyhexyl)-N-(4-ethynylphenyl)-pentandiamide (0.17 g, 0.52 mmol) is dissolved in CH$_2$Cl$_2$ (5 ml). 2-Cyanoethyl-N,N,N',N'-tetraisopropylphosphoramidite (0.19 g, 0.62 mmol) is added, followed by tetrazole (0.91 ml of 0.45M in acetonitrile) with vigorous swirling. The reaction solution is vortexed at room temperature for 3 hours. Methylene chloride (50 ml) is added to the reaction flask to increase the volume, and the crude solution is washed with 5% sodium bicarbonate/0.5% TEA (100 ml). The organic layer is dried over magnesium sulfate, filtered, concentrated, and co evaporated twice with acetonitrile (10 ml). The residue is dissolved in acetonitrile (5 ml) and dried over several granules of calcium hydride.

Example 3

Synthesis of Fluorescent DNA Using Ethynyl Modified DNA Probes and the Azidocoumarin Synthesis of DNA Probe functionalized with Ethynyl Aniline: A DNA probe (dT-20-mer) modified at its 5' loci with the ethynyl aniline is produced using the following procedure. The phosphoramidite, N'-(6-aminohexyl 2-cyanoethyl diisopropyl amidophosphite)-N-(4-ethynylphenyl)-pentandiamide, is introduced as the last step of automated phosphoramidite solid phase synthesis of a dT-20-mer. Preferably, a 0.3M solution of sulfur in anhydrous pyridine is used as an alternative to the Iodine/THF/Pyridine/Water solution typically used. The sulfurization reaction is performed for 30 min at room temperature. Standard protocols are used to release the DNA probe from the solid support and deprotection, such as, concentrated ammonia at elevated temperature (55° C.; 8 hr). Ammonia is evaporated under reduced pressure and the 5'-modified DNA probe V is purified by RP HPLC. (C18 Dionex column, 0.1 MTEAA/Acetonitrile; gradient 1% acetonitrile/min).

Synthesis of the Coumarin-Azido Derivative: The synthesis of 3-azido-7-diethylaminocoumarin is accomplished using appropriately modified procedures as described in the supporting information of Wang at al., Organic Letter, 2004, 6(24), 4603-4606. Generally, 4-diethylamino salicyl aldehyde and nitroacetate react to give the nitro-derivative which is reduced giving the amino-derivative which is converted into the corresponding azido-derivative.

Synthesis of Fluorescent DNA using Ethynyl Modified DNA Probes and the Azidocoumarin: DNA Probe functionalized with Ethynyl Aniline and 3-azido-7-diethylaminocoumarin are mixed under conditions described in Sharpless at al., Angew. Chem. Int. Ed., 2002, 41(14), 2596. Generally, both the DMSO/water and Ethanol/water mixtures are used as a solvent systems at ambient or at elevated temperatures. Preferably, the reaction is facilitated by the addition of copper (II) sulfate pentahydrate. Under more preferred conditions the DNA Probe functionalized with Ethynyl Aniline (0.5 mmol) is reacted with 100-fold excess of 3-azido-7-diethylaminocoumarin in 200 µl of water/EtOH (3:1) in the presence of sodium ascorbate and copper (II) sulfate pentahydrate. The reaction mixture is stirred in the dark at room temperature for 24 hours. The unreacted 3-azido-7-diethylaminocoumarin is subsequently removed by size exclusion chromatography and the final DNA conjugate is purified by RP HPLC chromatography using C18 RP column and 0.1M TEAA/Acetonitrile as a mobile phase (gradient 1% of Acetonitrile per min)

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A method for conjugating a first-biomolecule molecule to a second molecule comprising reacting a first molecule, said first molecule comprising or linked to an alkynyl group, with a second molecule, said second molecule comprising or linked to an azide group, under conditions wherein said first molecule and said second molecule are conjugated together, wherein said first molecule has the formula:

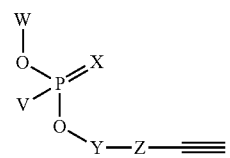

wherein W is biomolecule; X is O or S, V is O or a phosphate protecting group, Y is absent or a linking group and Z is absent or comprises an aryl group.

2. The method of claim 1, wherein said biomolecule comprises a nucleotide.

3. The method of claim 1, wherein said biomolecule comprises a nucleic acid.

4. The method of claim 1, wherein said first molecule comprises a label.

5. The method of claim 4, wherein said label is selected from the group consisting of a dye, a radiolabel, a hapten, a binding moiety, a lumogenic moiety, a phosphorescent moiety, a fluorophore, a chromophore, a mass tag and a particle.

6. The method of claim 4, wherein said label is a fluorescent label.

7. The method of claim 1, wherein said first molecule is affixed to a solid support.

8. The method of claim 1, wherein said alkynyl group is an ethynyl group.

9. The method of claim 1, wherein said second molecule comprises a biomolecule.

10. The method of claim 9, wherein said biomolecule comprises a nucleotide.

11. The method of claim 9, wherein said biomolecule comprises a nucleic acid.

12. The method of claim 1, wherein said second molecule comprises a label.

13. The method of claim 12, wherein said label is selected from the group consisting of a dye, a radiolabel, a hapten, a binding moiety, a lumogenic moiety, a phosphorescent moiety, a fluorophore, a chromophore, a mass tag and a particle.

14. The method of claim 12, wherein said label is a fluorescent label.

15. The method of claim 1, wherein said second molecule is affixed to a solid support.

* * * * *